US00PP37848P2

(12) United States Plant Patent
Dirr et al.

(10) Patent No.: US PP37,848 P2
(45) Date of Patent: Nov. 17, 2026

(54) ***FOTHERGILLA* PLANT NAMED 'Malone'**

(50) Latin Name: *Fothergilla intermedia*
Varietal Denomination: Malone

(71) Applicant: Premier Introductions Inc, Watkinsville, GA (US)

(72) Inventors: Michael Dirr, Bogart, GA (US); Mark Griffith, Watkinsville, GA (US); Jeff Beasley, Lavonia, GA (US)

(73) Assignee: Premier Introductions Inc., Watkinsville, GA (US)

( * ) Notice: Subject to any disclaimer, the term of this patent is extended or adjusted under 35 U.S.C. 154(b) by 0 days.

(21) Appl. No.: 19/459,712

(22) Filed: Jan. 26, 2026

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP32,049 P2 * 8/2020 McGowan ..... A01H 5/12 Plt./226

* cited by examiner

*Primary Examiner* — Susan Mccormick Ewoldt

(57) ABSTRACT

A new and distinct cultivar of *Fothergilla* plant named 'Malone' is disclosed, characterized by its by its upright, oval to rounded habit with dense branching, abundant, showy white flowers in the spring, and glossy dark green summer foliage with attractive multi-colored maroon to brilliant red fall color. The new cultivar is a *Fothergilla*, typically produced as an outdoor ornamental plant.

6 Drawing Sheets

Genus and species of plant claimed: *Fothergilla intermedia.*

Variety denomination: 'Malone'.

BACKGROUND OF THE INVENTION

The present invention comprises a new and distinct *Fothergilla* cultivar hereinafter referred to by the cultivar name 'Malone'. This new *Fothergilla* was a chance seedling found at a nursery in Good Hope, GA. Various *Fothergilla intermedia* plants were present in the field where the new cultivar was discovered, therefore the parents cannot be accurately identified.

'Malone' has been asexually reproduced by softwood cuttings since 2021 in Watkinsville, GA. The characteristics of the cultivar have been stable and reproduced true to type in successive vegetative generations.

SUMMARY OF THE INVENTION

'Malone' has not been observed under all possible environmental conditions. The phenotype may vary somewhat with changes in light, temperature, soil and rainfall without, however, any variance in genotype.

The following traits have been observed and represent the characteristics of the new cultivar. These characteristics in combination distinguish 'Malone' as a new distinct cultivar.

1. A upright, oval to rounded habit with dense branching.
2. Abundant, fragrant, showy white flowers in the spring.
3. Glossy dark green summer foliage with attractive multi-colored fall foliage, initiating maroon and maturing to brilliant red.

COMMERCIAL COMPARISON

'Malone' can be distinguished from *Fothergilla* 'Mt. Airy' (unpatented) by its smaller leaves and compactness.

'Mt. Airy' has larger leaves and is not compact. 'Mt. Airy' has matte dark green leaves. 'Malone' has foliage that is glossy dark green in summer, it consistently turns rich maroon to red in the fall. 'Mt. Airy' has fall color that is consistently mottled yellow, orange, and red 'Malone' is similar to *Fothergilla intermedia* 'Alice' (U.S. Plant Pat. No. 32,049). 'Alice' has leaves that are matte blue green. 'Malone' has glossy dark green summer color. In the fall 'Malone' turns rich maroon then to brilliant red, but 'Alice' produces a mixture of yellow, orange, and red fall colors.

BRIEF DESCRIPTION OF THE DRAWINGS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Fothergilla.*

DETAILED DESCRIPTION

Figure 1:
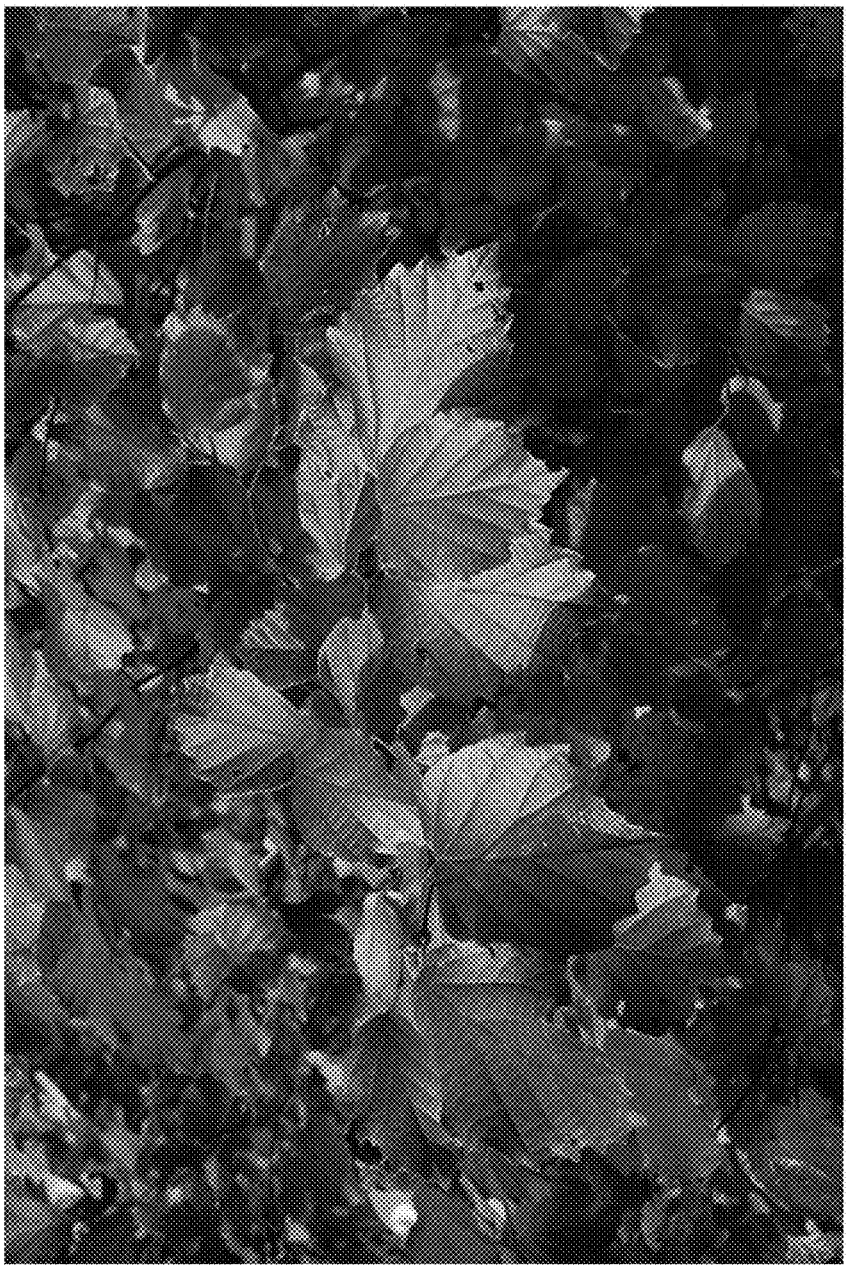
FIG. 1 shows the initial (opening) maroon fall color on the original plant.
Figure 2:
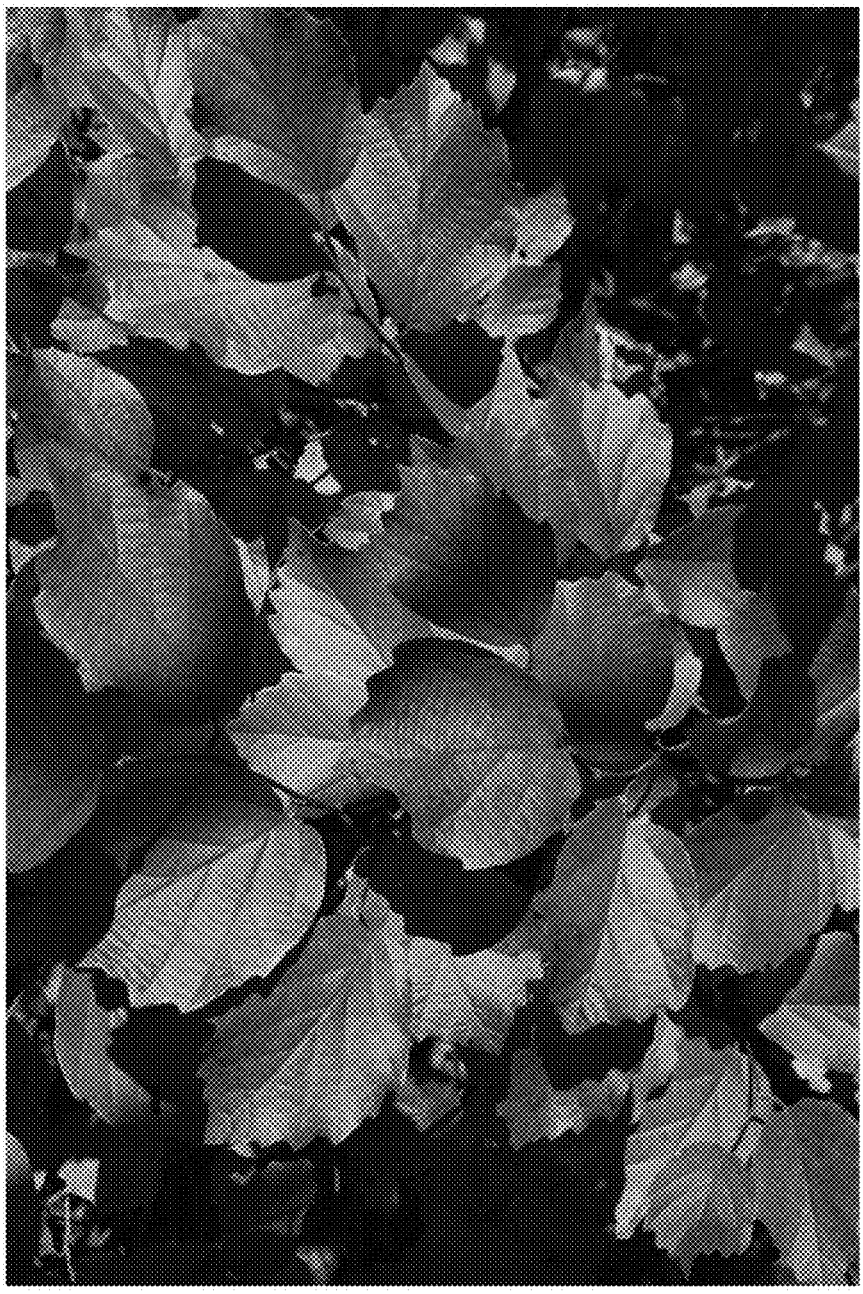
FIG. 2 shows the red fall color as the foliage matures.
Figure 3:
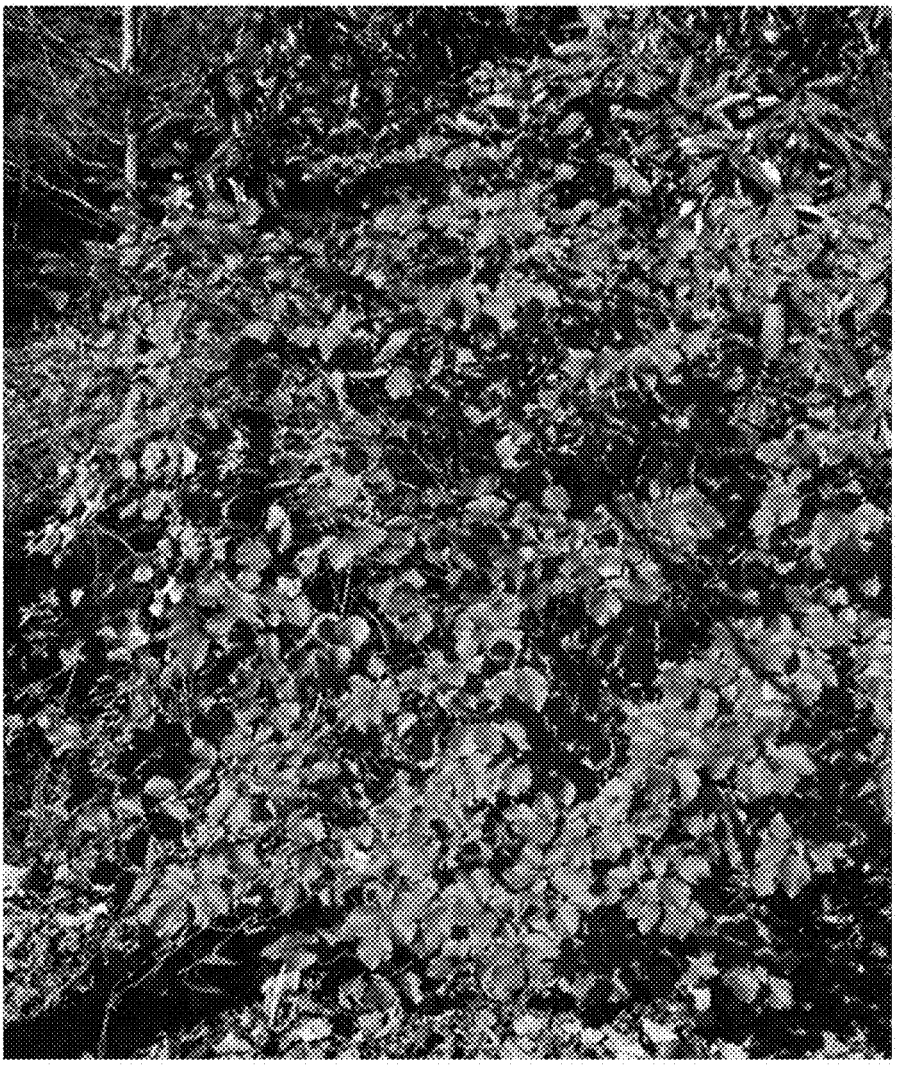
FIG. 3 shows the original plant with red fall color.
Figure 4:
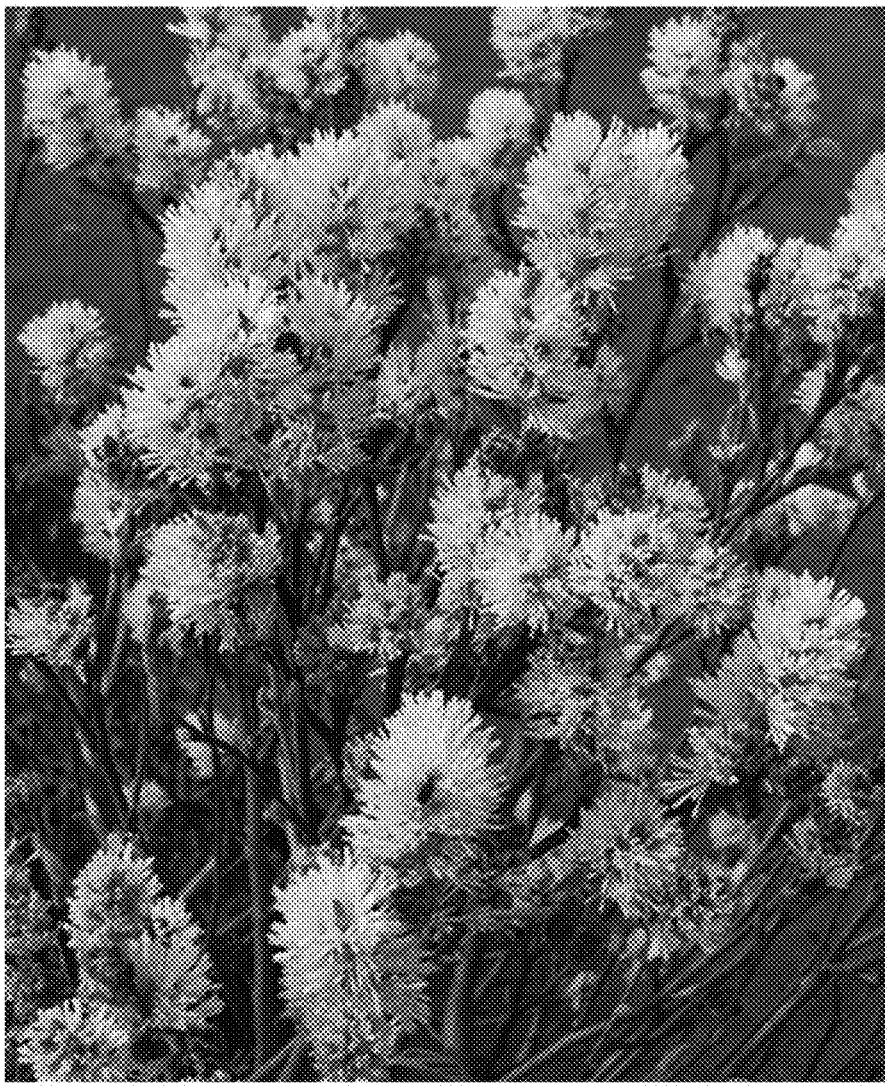
FIG. 4 shows a close-up view of flowers on a 3-year-old plant.
Figure 5:
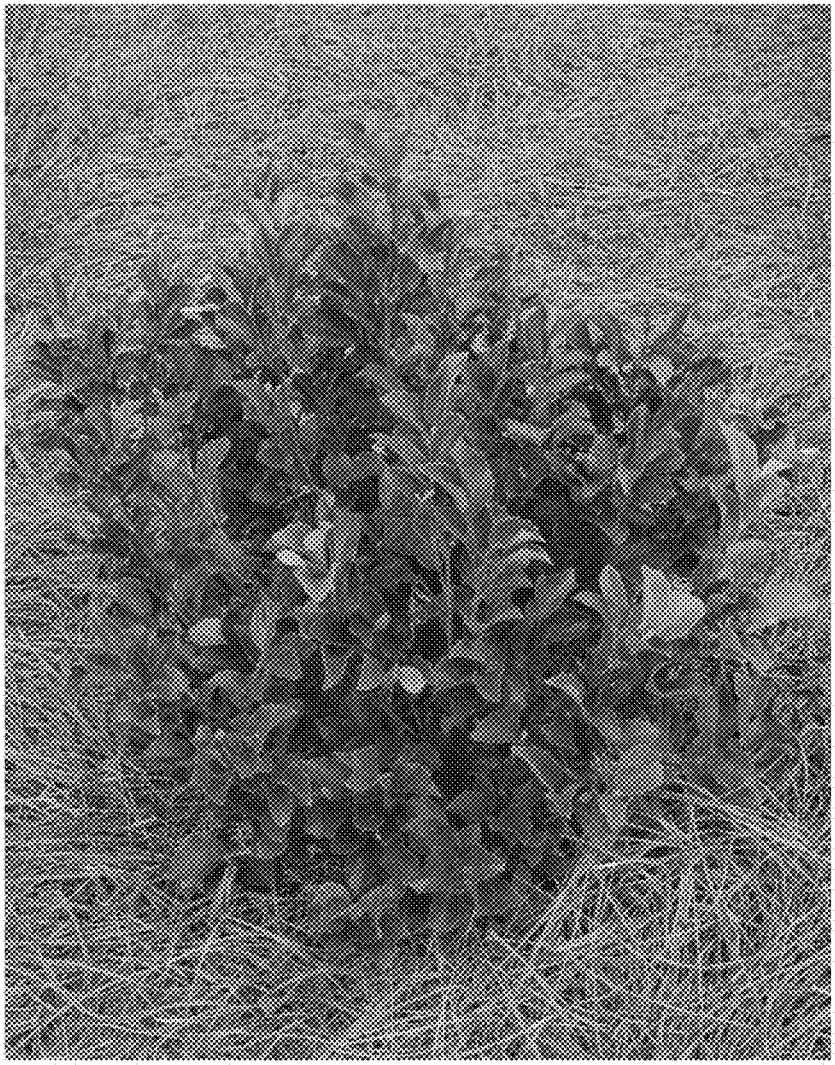
FIG. 5 shows the plant habit of a 3-year-old plant.
Figure 6:
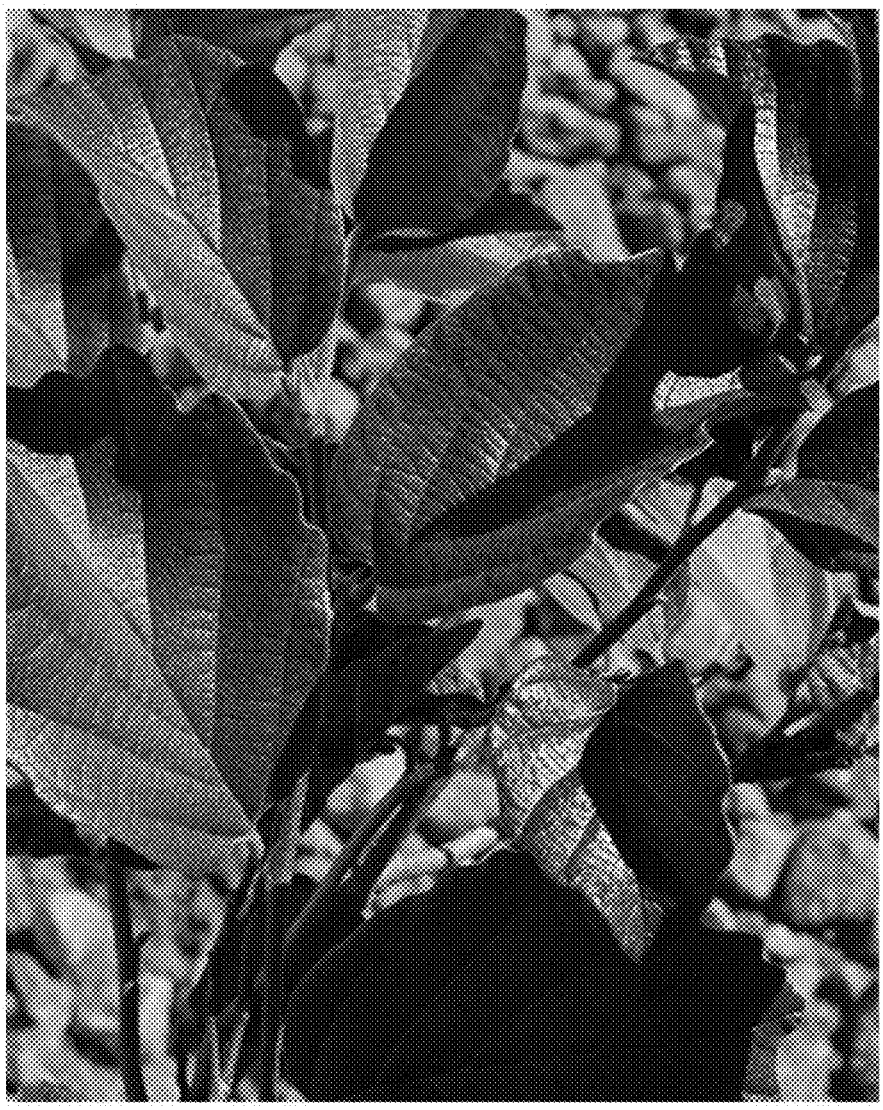
FIG. 6 shows the glossy dark green summer foliage on a 3-year-old plant.

In the following description, color references are made to The Royal Horticultural Society Colour Chart, 2015 Edition, except where general terms of ordinary dictionary significance are used. Plants used for the description were grown in the ground under outdoor conditions in a nursery in Watkinsville, GA. Plants were about three years old when the description was recorded.

Botanical classification: 'Malone' is a cultivar of *Fothergilla intermedia.*

Propagation: Soft-wood cuttings. Time to initiate roots about 5 weeks at 18° C.-27° C. Time to produce a rooted liner in summer about 3 months.

Plant description: The claimed variety is a deciduous shrub with an upright and outward growth habit. The original plant, now about 3-years-old in the ground, is about 180 cm in height from the soil level to the top of the inflorescences, and about 150 cm in diameter.

*Freely branching.*—Pinching enhances branching. Stems (current year's growth) Color: 199A. Texture: Pubescent. Stems (prior year's growth) Color: 197B.

*Branches* (*primary lateral branches*).—Length 25 cm. Quantity: 15. Diameter: 3 mm. Color 197B. Texture: Glabrous with vertical fissures of Grey 201C. Aspect: Straight branches occurring on average 45° from center of the plant. Strength: strong.

*Root description.*—Numerous, fine, fibrous and well-branched. Color: NN155C.

Leaves:

*Leaf.*—Arrangement: Alternate, simple. Length 4.5 cm. Width 3.4 cm. Shape of blade: Broad elliptic. Apex: Acute. Base: Obtuse. Margin: Crenate. Texture of top surface: Leathery. Texture of bottom surface: Rough, powdery rigid veins. Pubescence: None.

*Color.*—Young foliage upper side: 136B. Young foliage under side: 138A. Mature foliage: upperside: 137B. Lower surface: 137D. Fall foliage a range of colors including: 30A, 180A, and 183D.

*Venation.*—Pinnate. Vein color, upper surface: 137C. Lower surface 143C.

*Petiole.*—About 5 mm. Diameter: about. 1 mm. Color: 137C. Texture: Pubescent.

Flowers:

*Inflorescence.*—Terminal spikes of brush-like, apetalous flowers composed of numerous showy stamens. Number of inflorescences per plant about 100. Number of flowers per inflorescence about 23. Flowering season late March to mid-April in Watkinsville, GA. Fragrance: fragrant. Inflorescence: Length: 3 cm. Diameter: 2 cm. Flower (stamens) length: about 1 cm. Diameter: about 0.5 cm. Depth: 1 cm.

*Flower bud shape.*—Oblong. Length: 0.8 cm. Diameter: 0.6 cm. Color: 144A with bracts of N199C.

*Petals.*—None.

*Sepals.*—Quantity: 5. Appearance: small. Texture: Pubescent. Arrangement: Whorled. Shape: Elliptic. Length: 5 mm. Width: 3 mm. Tip: Obtuse. Base: Truncated. Margin: Entire, pubescent. Color: Upper and Lower side: 144A to 177A.

*Peduncle.*—Length 1 cm. Diameter: 3 mm. Color: 145A. Texture: Pubescent.

*Pedicels.*—None.

*Calyx.*—Shape: Star-like. Length 1 cm. Diameter: 1 cm.

*Reproductive organs.*—Gynoecium: Pistil number: 1. Pistil length: 1 cm. Stigma shape: Linear. Stigma color: 155C. Androecium: Stamen number: average about 23 (per flower). Approximately 185 per spike. Filament length: 1 cm. Filament diameter: 1 mm at apex, tapering to base. Filament color: 155A. Anther shape: Bilobed. Anther size: less than 1 mm. Anther color: 10A. Amount of pollen: average. Pollen color: 10A.

Fruit:

*Fruit and seed.*—None Observed.

Plant hardiness:

*Plant hardiness.*—USDA Hardiness Zone Map (2023): Zones 4-8.

Disease/pest resistance: Susceptibility or resistance to diseases beyond that typically found in other *Fothergilla intermedia* plants have not been observed.

What is claimed is:

1. A new and distinct cultivar of *Fothergilla* plant named 'Malone' as herein illustrated and described.

* * * * *